United States Patent [19]
Zahedi

[11] Patent Number: 5,702,475
[45] Date of Patent: Dec. 30, 1997

[54] MODULAR BONE IMPLANT WITH PAN AND PINS

[76] Inventor: Amir Zahedi, Birkenweg 16, D-48155, Münster, Germany

[21] Appl. No.: 601,170

[22] Filed: Feb. 14, 1996

[51] Int. Cl.$^6$ ............................................. A61F 2/34
[52] U.S. Cl. ........................................ 623/22; 623/18
[58] Field of Search ........................ 623/16, 18, 19, 623/20, 22, 23

[56] References Cited

U.S. PATENT DOCUMENTS

| | | | |
|---|---|---|---|
| 3,658,058 | 4/1972 | Tronzo | 623/22 |
| 3,781,918 | 1/1974 | Mathys | 623/22 |
| 4,955,917 | 9/1990 | Karpf | 623/22 |

FOREIGN PATENT DOCUMENTS

| | | | |
|---|---|---|---|
| 0013863 | 8/1980 | European Pat. Off. | 623/22 |
| 2519545 | 7/1983 | France | 623/23 |
| 2598908 | 11/1987 | France | 623/22 |
| 2638963 | 5/1990 | France | 623/22 |
| 2807289A1 | 8/1979 | Germany . | |
| 4205018C1 | 8/1993 | Germany . | |
| 1483938 | 8/1977 | United Kingdom . | |
| 2207606 | 2/1989 | United Kingdom | 623/22 |
| 4005234 | 3/1994 | WIPO | 623/22 |

*Primary Examiner*—David Isabella
*Attorney, Agent, or Firm*—Lahive & Cockfield, LLP

[57] ABSTRACT

In a bone implant with a pan that is designed so that it is mainly in the form of a segment of a sphere for receiving the head of a femoral bone prosthesis, and with pin-type fastening means for anchoring the pan in the hip bone of the patient. The pan further includes recesses to receive the fastening means. In order to create a modular pan replacement, the recesses are designed for an axially parallel arrangement of the fastening means, and the recesses can be provided with stops to prevent movement of the fastening means towards the interior of the pan. The fastening means are threadless in the area which is inserted into the hip bone of the patient.

6 Claims, 1 Drawing Sheet

MODULAR BONE IMPLANT WITH PAN AND PINS

The invention relates to a bone implant according to the preamble of Claim 1.

BACKGROUND OF THE INVENTION

Bone implants of this kind are known for example from FR 2 598 908 A1. They comprise pins that are axially parallel and permanently shaped to the pan as well as bores through which screws can be screwed from the interior of the pan into the bone tissue of the patient to anchor the pan.

It is disadvantageous in this regard that the fastening means designed as screws can be pressed inward in the course of time and can result in abrasion of a plastic shell that has been inserted into the interior of the pan. This abrasion firstly leads to premature wear and secondly can cause inflammation so that a second operation becomes necessary at an undesirably early point in time.

The considerable difference in diameter between the screw head and the screw shaft results in a concentration of stress at the transition between these two different diameters, so that depending on the stresses that develop, damage to the screws can occur in this area that can destroy them, and this in turn can result in loosening of the prosthesis as well as abrasion of plastic and/or metal, so that this also can make undesirably early second operations necessary.

The provision of pins that are closely shaped to the pan does not correspond to the individual situation of each patient, so that the pins cannot be arranged individually in areas where the bone substance of the patient is most suitable for anchoring a prosthesis.

Bone implants that do not belong to the species are known for example as so-called "press-fit pans," an example of each is described in DE 42 05 018 C1 for example. The exact seating of the pan in the bone of the patient is achieved by a precise adjustment of the bone to the pan to be received.

In such bone implants that are not of this species, the fastening means are arranged so that they diverge. The problem therefore arises that when the first fastening screw is tightened, the pan is stressed eccentrically and shifts with respect to the ideal position it had initially assumed. The exact reception of the pan in the bone cavity is thus affected adversely. This problem is known in practice and thus the holes for receiving additional mounting screws are not drilled until the previous mounting screw has been fitted and anchored in the bone.

The goal of the invention is to improve a bone implant according to the species in such fashion that during the operation it can be fastened individually to each patient and does not exhibit any wear, or wear that is considerably reduced, during use by the patient.

SUMMARY OF THE INVENTION

This goal is attained by the bone implant, of the present invention.

In other words, the invention proposes that no pins permanently attached to the pan be provided, but that pins be used that can be inserted into the pan from the exterior and can be positioned individually in a manner that is most suitable for the individual bone structure. In addition, penetration of the pins into the interior of the pan under impact is ruled out, so that no abrasion of the components located inside the pan can be caused by pins that project too far inward.

Advantageously, the recesses can be made as axially parallel bores. This allows the pan to be manufactured economically. It also simplifies handling by comparison with one possible solution in which the recesses themselves are not axially parallel and in which specially shaped pins must be used in order to produce an axially parallel arrangement of the pins inserted into the pan.

A simple assembly of the pins within the pan can be achieved by making the bores converge conically toward the interior of the pan, into which bores suitably conical and nonthreaded sections of the pins can be forced.

The conical seat firstly ensures reliable securing of the pins when they are inserted, with the connection between the pin and the pan being improved by the counterpressure that develops when the pan is fitted. This counterpressure is achieved in practice by dimensioning the holes drilled for the pins so that the pins can be pushed into the drilled holes only when a certain pressure is developed.

A conical contact area between the pin and the pan, in contrast to a thread, ensures that no rubbing or grinding movement is required between the pin and the pan during preparation for the operation, so that metal abrasion can be eliminated as a result.

Advantageously, the pins can be of different lengths. In this manner, a more individual design is possible for the pan in which the pins are selected by length and are used where they will provide the optimum grip in the pelvic bone of the patient.

Advantageously, the number of recesses in the pan can be greater than the number of pins that is usually used in a pan. It is disadvantageous to provide a pan with a great many pins or, in the current prior art, with a very large number of screws, since the bone tissue holding the pan can be weakened as a result. Nevertheless it is advantageous to make the number of recesses larger than the number of pins that is expected to be used, because the adaptability and individualization capability of the bone implant is increased as a result, inasmuch as the fastening means can be located in each individual case to permit optimum retention of the bone implant.

Finally, it is advantageous according to the invention to arrange the pins in the direction that corresponds to the insertion direction of the bone implant. It is thus possible, in the manner described, initially to fit the pan with pins and then mount it on the pelvic bone of the patient. If the lengthwise direction of the pins differed from the insertion direction of the pan, the pan would first have to be fitted and then the pins would have to be inserted from the inside through the pan into the bone of the patient, with spring-elastic locking means then being required to form the stops that would support the movement of the pins into the interior of the pan, and absorb movement.

Embodiments of the invention will now be described in greater detail with reference to the drawings.

DESCRIPTION OF ILLUSTRATED EMBODIMENTS

Figure 1:
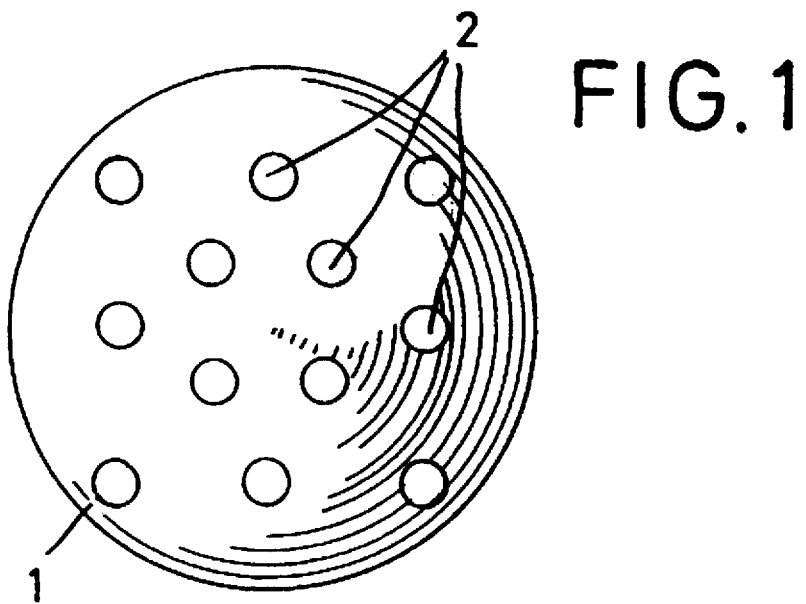
FIG. 1 is a top view of a pan.

In FIG. 1, a pan is numbered 1 which can be inserted into a pelvic bone of a patient and is designed as a so-called "press fit pan". Pan 1 has a plurality of axially parallel bores 2 that converge conically, into which fastening means can be inserted.

Figure 2:
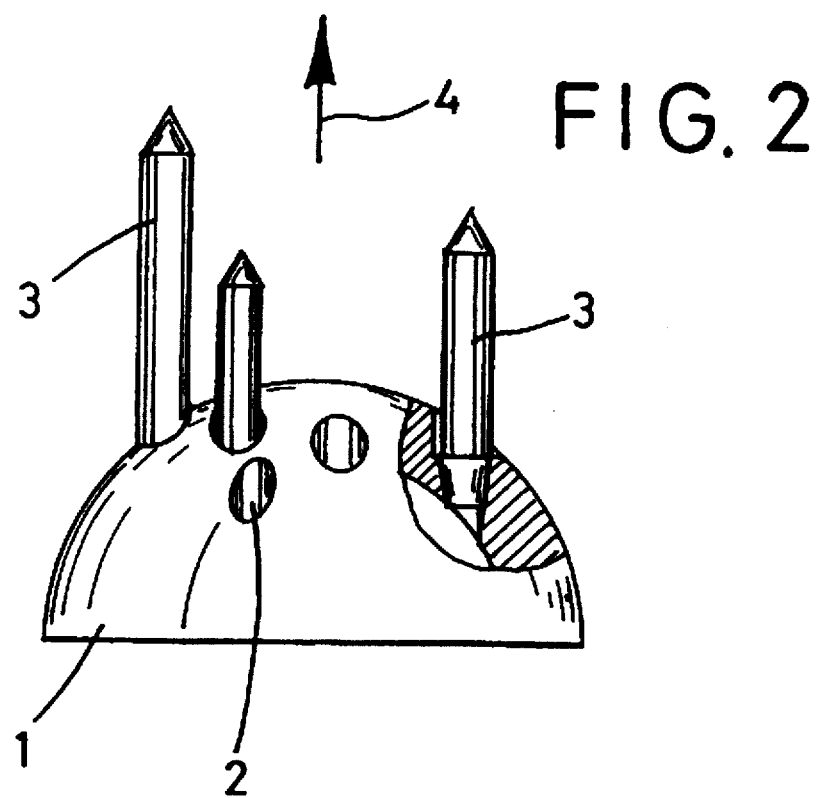
FIG. 2 is a side view of a pan similar to that in FIG. 1, with certain areas of the pan shown cut away.

As is evident from FIG. 2, the fastening means are designed as pins 3. Pins 3 are all made without threads and have a conical lower part by which they can be inserted into the bores 2 in pan 1.

To adapt to existing conditions for each individual patient, pins 3 of various lengths are selected so that the population of bores 2 with a very wide variety of pins 3 is possible as a function of the conditions prevailing in each patient.

The numeral 4 in FIG. 2 indicates the insertion direction in which pan 1 is inserted into the pelvic bone of the patient. It is then evident that the axial direction of both pins 3 and bores 2 runs parallel to insertion direction 4.

Pan 1 and pins 3 is inserted as follows into the pelvic bone of the patient:

Initially a cavity to receive pan 1 is milled into the pelvic bone of the patient, as is known from the prior art. Then, using a suitable drilling guide, a number of bores are drilled into the pelvic bone of the patient to receive pins 3 later on, with the optimum arrangement and depth of the bores being determined with the aid of x-rays.

The depth of each bore that is made can be checked and confirmed with the aid of instruments known in the prior art.

After pan 1 is populated in the manner provided with pins 3, pan 1 together with pins 3 can be inserted into the pelvic bone of the patient. In particular, when the diameter of the bores in the pelvic bone of the patient is slightly smaller than the diameter of pins 3, a pressure develops that anchors pins 3 in bores 2 of pan 1 with increasing strength.

In general the length of time required to prepare for the insertion and to perform the actual insertion of pan 1 and pins 3 into the pelvic bone of the patient is relatively short and correspondingly considerate of the patient.

When pan 1 has been inserted into the pelvic bone of the patient, protection for the patient is also provided by virtue of the fact that the conical design of bores 2 prevents pins 3 from entering the interior of pan 1, even if pins 3 should loosen in the pelvic bone of the patient or if pan 1, because of a strong compressive stress, should work its way into the interior of the pelvic bone.

In any event, the possibility is excluded of pins 3 being able to enter the interior of pan 1 or of being able to project there to the extent that they could lead to an abrasion of an inner shell that may be provided as a sliding shell inside pan 1. Since abrasion particles are prevented in this manner, that could lead to local inflammation, with the possibility of the bone tissue being attacked by said inflammation, the pan according to the invention protects the patient not only at the time it is fitted to the patient but also later when it is worn.

When the bone implant is removed, either pins 3 together with pan 1 are pulled out of the pelvic bone of the patient, when there is a firm connection between pins 3 and pan 1 because of the conical seat, or pins 3 are left in the bone substance when the retaining forces there are greater than in the vicinity of bores 2. In this case the conical areas of pins 3 that project freely from the bone cavity can be gripped with suitable pliers and pulled out after pan 1, and possibly one or more pins permanently connected thereto, has been pulled out in a direction opposite to the insertion direction 4.

I claim:

1. A bone implant comprising a pan having an outer surface configured in a form of a segment of a sphere and an inner surface configured to receive a head of a femoral prosthesis, and pin-type fastening means to anchor the pan in the pelvic bone of the patient, the pan having recesses sized to receive the fastening means, and with the recesses being designed for an axially parallel arrangement of the fastening means, characterized in that the recesses have axially parallel bores, each said bore converging conically toward an interior of the pan, and wherein said fastening means have a conically-shaped portion for insertion into said pan, and stop means for preventing movement of the fastening means towards the interior of the pan, said fastening means being substantially free of threads in an area that is inserted into the pelvic bone of the patient.

2. Bone implant according to claim 1 characterized in that said fastening means includes a plurality of pins having different lengths.

3. Bone implant according to claim 1 characterized in that the number of recesses is greater than the number of fastening means.

4. Bone implant according to claim 1 characterized in that said recesses and said pins (2) each have a lengthwise axis that extend parallel to the insertion direction (4) of pan (1).

5. A bone implant for insertion within the pelvic bone of a patient, comprising a pan portion having a substantially hemispherical shape forming an interior cavity, said pan portion having a plurality of recesses that extend between an outer surface and an inner surface of the pan portion, and a plurality of fastener elements having a head portion and an outwardly extending shaft, said shaft being substantially free of threads along a portion of the shaft that is adapted to seat within the pelvis of the patient, said recesses having a conically-shaped taper converging towards the inner surface of the pan portion for preventing at least one of said fastener elements when mounted within one of the recesses from being forced from said recess into said interior cavity.

6. The bone implant of claim 5 wherein said recesses extend parallel to a central axis of said pan such that said recesses are parallel to one another.

* * * * *